(12) United States Patent
Malhotra et al.

(10) Patent No.: US 10,912,734 B2
(45) Date of Patent: Feb. 9, 2021

(54) DEPOT FORMULATION

(71) Applicant: Cipla Limited, Mumbai (IN)

(72) Inventors: Geena Malhotra, Mumbai (IN); Sarabjit Singh, Mumbai (IN)

(73) Assignee: Cipla Limited, Mumbai (IN)

(*) Notice: Subject to any disclaimer, the term of this patent is extended or adjusted under 35 U.S.C. 154(b) by 0 days.

(21) Appl. No.: 16/412,612

(22) Filed: May 15, 2019

(65) Prior Publication Data

US 2019/0350844 A1 Nov. 21, 2019

(30) Foreign Application Priority Data

May 16, 2018 (IN) .............................. 201821018318

(51) Int. Cl.
| | | |
|---|---|---|
| *A61K 9/00* | (2006.01) | |
| *A61K 31/55* | (2006.01) | |
| *A61K 47/10* | (2017.01) | |
| *A61K 47/14* | (2017.01) | |
| *A61K 47/44* | (2017.01) | |
| *A61P 25/34* | (2006.01) | |
| *A61K 47/46* | (2006.01) | |
| *A61K 47/34* | (2017.01) | |
| *A61K 47/32* | (2006.01) | |
| *A61K 47/38* | (2006.01) | |
| *A61K 47/26* | (2006.01) | |

(52) U.S. Cl.
CPC ............ *A61K 9/0024* (2013.01); *A61K 31/55* (2013.01); *A61K 47/10* (2013.01); *A61K 47/14* (2013.01); *A61K 47/26* (2013.01); *A61K 47/32* (2013.01); *A61K 47/34* (2013.01); *A61K 47/38* (2013.01); *A61K 47/44* (2013.01); *A61K 47/46* (2013.01); *A61P 25/34* (2018.01)

(58) Field of Classification Search
None
See application file for complete search history.

(56) References Cited

U.S. PATENT DOCUMENTS

| | | |
|---|---|---|
| 2004/0235850 A1 | 11/2004 | Waterman |
| 2006/0084656 A1 | 4/2006 | Ziegler et al. |
| 2008/0181933 A1 | 7/2008 | Johnson et al. |
| 2011/0086086 A1* | 4/2011 | Johnson ............... A61K 9/0014 424/449 |
| 2013/0144250 A1* | 6/2013 | Schwarz ............... A61K 9/0024 604/500 |

FOREIGN PATENT DOCUMENTS

WO 2007001296 A1 1/2007

* cited by examiner

*Primary Examiner* — Brian J Davis
(74) *Attorney, Agent, or Firm* — Meunier Carlin & Curfman LLC

(57) ABSTRACT

A pharmaceutical long acting depot composition is provided as an aid to smoking cessation treatment. The formulation comprises a therapeutically effective amount of varenicline or its pharmaceutically acceptable derivative and pharmaceutically acceptable excipients. The process of preparation of the formulation is also provided.

17 Claims, No Drawings

DEPOT FORMULATION

CROSS REFERENCE TO RELATED APPLICATIONS

This application claims priority to co-pending Indian Provisional Patent Application Serial Number 201821018318 filed on May 16, 2018, the contents of which are hereby incorporated by reference in its entirety.

FIELD OF INVENTION

The present invention relates to depot formulation comprising varenicline, or pharmaceutically acceptable salts thereof, and pharmaceutically acceptable excipients. The present invention also relates to processes for making such a formulation and use of the said formulation as an aid to smoking cessation treatment.

BACKGROUND OF INVENTION

Smoking is the leading preventable cause of death worldwide. Smoking-related diseases kill an estimated 438,000 Americans each year, including those affected indirectly, such as premature babies of smoking mothers and victims of 'secondhand' smoke. Millions of people in the world have at least one serious illness caused by smoking. Smoking causes chronic lung disease, cardiovascular disease and stroke. Smoking may be a cause of several cancers (in addition to lung cancer) and has been linked to slowed healing of wounds, infertility and stomach ulcers.

Many factors make quitting smoking difficult. Most smokers trying to quit fail several times before they are able to break the habit. Smokers who are trying to quit are faced with social influences that may persuade them to conform and continue smoking. Cravings are easier to detain when one's environment does not provoke the habit. If a person who stopped smoking has close relationships with active smokers, he or she is often put into situations that make the urge to conform more tempting. For example, if an acquaintance offers a cigarette as a polite gesture, the person who has stopped smoking will be more likely to break his commitment of quitting smoking. Smokers with major depressive disorder may be less successful at quitting smoking than non-depressed smokers. Thus, smoking is a notoriously difficult habit to break. Relapse (resuming smoking after quitting) can also happen which has been related to psychological issues such as low elf-efficacy, or non-optimal coping responses however, psychological approaches to prevent relapse have not been proven to be successful.

There are various methods of breaking the smoking habit. Smoking cessation therapies are more likely to succeed for patients who are motivated to stop smoking and who are provided additional advice and support. The patients are also provided with appropriate educational materials and counseling to support the quit attempt. Some methods involve medication alone. Most smokers who try to quit, do so without any assistance, however, only 3% to 6% of such attempts are successful. The simplest medication regimen involves administering nicotine in gradually diminishing doses. Nicotine patches or lozenges are used to quit smoking habit. The goal of these slow-release preparations is to maintain the subject in the comfort zone by keeping the blood nicotine concentration constant throughout the day. Over several weeks of treatment, the blood concentration of nicotine is gradually lowered. However, the person trying to quit smoking can easily remove the patches or stop taking lozenges if he or she gets demotivated to quit smoking leading to failure of the treatment.

Varenicline is the first line treatment approved by FDA for use as an aid to smoking cessation. It remarkably binds with high affinity and selectivity at $\alpha_4\beta_2$ neuronal nicotinic acetylcholine receptors which produces agonist activity, while simultaneously preventing nicotine binding to these receptors and this leads to efficacy of varenicline in smoking cessation. Varenicline decreases the urge to smoke and reduces withdrawal symptoms and may help in some relapsed smokers.

Varenicline is available commercially as CHANTIX, an oral immediate release tablet containing varenicline tartrate in the strength equivalent to 0.5 mg and 1 mg free base. The dosage regimen includes administering 0.5 mg once daily on days 1-3 and 0.5 mg twice daily on days 4-7. Once the dosing titration has been successfully completed, patients are advised to take 1 mg twice daily for an additional eleven weeks. Patients that successfully stop smoking under the regimen are advised to take an additional 12 week course of treatment to increase likelihood of long-term abstinence.

US 2006/0084656 provides an intranasal, buccal, sublingual or pulmonary dosage forms of varenicline.

US 2004/0235850 provides storage stable pharmaceutical dosage form of varenicline adducts with certain excipients.

US 2008/0181933 provides a chewing gum composition of varenicline comprising a water insoluble base portion and a water-soluble portion.

However, relative to an oral dosage form, delivery of varenicline via a transdermal composition would be a preferred choice by patients who have difficulty in swallowing tablets, capsules or other solids. Also, the tablet dosage form of varenicline can produce a certain level of nausea in patients. Thus, to reduce these side effects, transdermal composition of varenicline are also provided wherein a gradual release of the varenicline via skin layers might reduce the incidence of nausea and enhance the patient compliance and desirability of the drug to a larger patient population requiring its use.

WO 2007/01296 provides transdermal composition comprising varenicline or its pharmaceutically acceptable salt or prodrug form.

However, it is likely that if the person gets demotivated to quit smoking during the treatment and experience a strong urge to smoke, he or she will stop applying varenicline transdermal patch by removing it from the application site thereby discontinuing the treatment. Hence, adherence to varenicline transdermal patch treatment is often sub-optimal.

Thus, there is an unmet need to provide an alternate dosage form such as a depot formulation, which would provide higher compliance rate along with maintaining therapeutic levels of the drug in the patient's system for days or weeks at a time. A depot formulation may provide convenience for a patient in need of chronic medication. By delivering drug without exposure to the GI tract, the potential issue of drug degradation is also avoided. Moreover, a depot formulation may provide better compliance due to the infrequent dosing regimen and convenience.

Varenicline is therefore a good drug candidate for incorporation into sustained delivery devices, where the patients would be treated for long time periods with just one application. Hence, a drug delivery technology, especially depot preparations which can reduce the total number of such administration and maintain the plasma drug levels for longer time would be preferred. Such reduction in frequency of drug dosing in practice may be achieved by formulating injectable depot system that are capable of releasing drug in a slow but predictable manner and consequently improve patient compliance. Depot injections allow careful control of drug usage (as opposed to orally administered drugs), where overall treatment efficacy and/or side effects may be identified. Furthermore, it is easy to identify defaulters and prepare interventions. These long acting depot formulations of varenicline can have the potential to not only boost the therapeutic benefit in most cases, also reduce any unwanted events, such as reduce the risk of accidental or deliberated overdose and maintain a stable release rate for several weeks, several months or longer to avoid the drawbacks of oral administration such as nausea, poor bioavailability, high frequency of administration, possible toxicity and inadequate individualizable dosing. The long acting depot formulation of varenicline of the present invention can address the problems of fluctuating drug concentration and will provide continuous stimulation of receptors prolonging the duration of action and thus improving patient compliance.

OBJECT OF THE INVENTION

An object of the present invention is to provide a pharmaceutical long-acting depot composition comprising varenicline or its pharmaceutically acceptable derivatives having improved systemic absorption.

Another object of the present invention is to provide a long acting depot formulation comprising varenicline or its pharmaceutically acceptable salts and one or more pharmaceutically acceptable excipients.

Another object of the present invention is to provide a long acting depot formulation comprising varenicline or its pharmaceutically acceptable salts wherein the particle size of the drug is about 0.5-100 μm.

Another object of the present invention is to provide a process of preparing a long acting depot formulation comprising varenicline or its pharmaceutically acceptable salts and one or more pharmaceutically acceptable excipients.

Another object of the present invention is to provide an aid to smoking cessation treatment by administering a long acting depot formulation comprising varenicline or its pharmaceutically acceptable salt and one or more pharmaceutically acceptable excipients.

Another object of the present invention is to provide a method for reducing nicotine addiction, aiding in the cessation of, or lessening of, tobacco use in a subject by administering a long acting depot formulation comprising varenicline or its pharmaceutically acceptable salts and one or more pharmaceutically acceptable excipients.

SUMMARY OF THE INVENTION

According to an aspect of the present invention, there is provided a pharmaceutical long-acting depot composition comprising varenicline or its pharmaceutically acceptable derivatives having improved systemic absorption.

According to an aspect of the present invention, there is provided a long acting depot formulation comprising varenicline or its pharmaceutically acceptable salts and one or more pharmaceutically acceptable excipients.

According to second aspect of the invention, there is provided a long acting depot formulation comprising varenicline or its pharmaceutically acceptable salts wherein the particle size of the drug is about 0.5-100 μm.

According to third aspect of the present invention there is provided a process for preparing a long acting depot formulation comprising varenicline or its pharmaceutically acceptable salts and one or more pharmaceutically acceptable excipients.

According to fourth aspect of the present invention, there is provided an aid to smoking cessation by administering long acting depot formulation comprising varenicline or its pharmaceutically acceptable salts and one or more pharmaceutically acceptable excipients.

According to fifth aspect of the present invention there is provided a method for reducing nicotine addiction, aiding in the cessation of, or lessening of, tobacco use in a subject by administering a long acting depot formulation comprising varenicline or its pharmaceutically acceptable salts and one or more pharmaceutically acceptable excipients.

DETAILED DESCRIPTION OF THE INVENTION

Smoking cessation with varenicline involves administration of tablets of 0.5 mg and in a fixed schedule orally daily. For most drugs, such as varenicline, depending on the dose, it may be possible to reduce such administration frequency from daily to once or twice monthly or even longer (6 months). This will enable the person attempting to quit smoking to get continuous dose of varenicline providing more compliance and avoiding the chances of irregular doses.

Varenicline salt is freely soluble in water and varenicline base is practically insoluble in water. Thus, it is a critical aspect of present invention to provide a pharmaceutical formulation which will provide the therapeutic amount of varenicline or its pharmaceutically acceptable salt for a long duration of time by controlling the release rate to achieve the desired pharmacologic effect and improved systemic absorption. The inventors of present invention after rigorous experimentation considering the physicochemical properties of varenicline or its pharmaceutically acceptable salts and to achieve the desired pharmacokinetic profile of formulation for longer duration of time, provided a pharmaceutical long acting depot formulation comprising varenicline or its pharmaceutically acceptable salts with one or more pharmaceutically acceptable excipients.

The term "therapeutically effective amount" or "effective amount" is such that when administered, the pharmaceutical composition results in the inhibition of the systemic infection. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired.

The term "treatment" or "treating" of a disease, virus or condition refers to executing a protocol that may include administering one or more drugs to a patient, in an effort to alleviate signs or symptoms of the disease, virus or condition. Alleviation can occur prior to signs or symptoms of the disease, virus or condition appearing, as well as after their appearance. Thus, treating or treatment includes reducing, preventing or prevention of the disease, virus or condition. In addition, treating or treatment does not require complete alleviation of signs or symptoms, does not require a cure, and specifically includes protocols that have only a marginal effect on the patient.

The term "reduced initial burst release" as per the present invention means the reduction in release of active ingredient from the dosage form at initial time points. The release of active ingredient in first hour according to the present invention is less than 35%, less than 30%, less than 235%, less than 20%, less than 15%, less than 10%, less than 5%, or less than 1%. The formulations of the present invention are preferably injectable preparations. Injectable formulations of the present invention are typically formulated as aqueous suspensions. Sterile injectable formulations can be prepared according to techniques known in the art using suitable carriers, excipients, dispersing or wetting agents, and suspending agents. The injectable formulations may be sterile injectable suspensions in a nontoxic, parenterally acceptable diluent or solvent. Among the acceptable vehicles and diluents or solvents that may be employed are water for injection, isotonic dextrose solution, Ringer's solution, isotonic sodium chloride solution, and suitable aqueous solvents and the like useful and safe for parenteral administration. In addition, sterile fixed oils or fatty esters are conventionally employed as solvents or suspending media.

The term "parenteral" as used herein refers to routes selected from subcutaneous (SC), intravenous (IV), intramuscular (IM), intradermal (ID), intraperitoneal (IP) and the like.

The term "long acting" as used herein refers to a pharmaceutical depot formulation which provides prolonged, sustained or extended release of the varenicline or its pharmaceutically acceptable salt to the general systemic circulation of a subject or to local sites of action in a subject. This term may further refer to a pharmaceutical depot formulation which provides prolonged, sustained, controlled or extended duration of action (pharmacokinetics) of the active substance in a subject.

The term "pharmaceutical depot formulation" or "long acting depot formulation" includes injection preparations, such as liquid dosage forms (liquids, liquid dispersions, suspensions, solutions, emulsions), gels, implants (rods, rings), biodegradable or non-biodegradable microparticles/microspheres in the form of controlled release formulations, lyophilized formulations, delayed release formulations, extended release formulations, pulsatile release formulations, and mixed immediate release and controlled release formulations etc. may also be envisaged under the ambit of the invention.

The term "biodegradable" as used herein refers to a component which erodes or degrades at its surfaces over time due, at least in part, to contact with substances found in the surrounding tissue fluids, or by cellular action.

Varenicline, which is the generic name for 7,8,9,10-tetrahydro-6,10-methano-6H-pyrazino [2,3-h] [3]-benzazepine, (2R,3R-dihydroxybutanedioate, has the following structure:

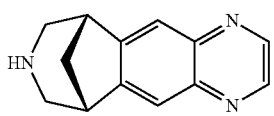 [SMILES: c1cnc2cc3c(cc2n1)[C@@H]1CNC[C@H]3C1]

The term "varenicline" is used in broad sense to include not only "varenicline" per se but also its pharmaceutically acceptable salts, pharmaceutically acceptable solvates, pharmaceutically acceptable hydrates, pharmaceutically acceptable enantiomers, pharmaceutically acceptable esters, pharmaceutically acceptable derivatives, pharmaceutically acceptable hydrate, pharmaceutically acceptable polymorphs, pharmaceutically acceptable isomer, pharmaceutically acceptable tautomer, pharmaceutically acceptable anhydrate, pharmaceutically acceptable prodrugs, pharmaceutically acceptable complexes etc.

The present invention provides long acting depot formulations comprising a therapeutically effective amount of varenicline base. In some embodiments, the pharmaceutical depot compositions may comprise any other pharmaceutically acceptable salt of varenicline including, but not limited to, sulfate, pyrosulfate, bisulfate, sulfite, bisulfate, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Preferred salts include tartrate, succinate, fumarate, chloride and sulfate, preferably the tartrate. In certain embodiments, the depot formulations contain varenicline as the free base.

Preferably, the disclosed depot formulations containing varenicline or its acceptable salt may be administered to the subject in need thereof once in every three days, once weekly, once in every two weeks, once a month, once in every two months, once in every three months, or once in every 6 months. In particular, the long acting depot formulation of the present invention provide a dosing regimen which ranges from once in three days to once every 6 months.

In some embodiments, the dose of varenicline ranges from about 0.05 mg to about 5 mg per day, from about 0.1 mg to about 5 mg per day, from about 0.25 mg to about 2.5 mg per day, from about 0.5 mg to about 2.5 mg per day, or from about 1 mg to about 2.5 mg per day. In an embodiment, the typical recommended monthly dosage regimen ranges from about 1.0 mg to about 200 mg. The depot formulations disclosed herein can deliver a daily therapeutic dose of varenicline for a period of at least 1 week, at least 2 weeks, at least 4 weeks, at least 8 weeks, or at least 12 weeks. In some cases, the depot formulation is designed to deliver a therapeutic dose of varenicline for a period of about 2 weeks, about 4 weeks, about 8 weeks, about 11 weeks, or about 12 weeks.

In some persons, some neuro-psychiatric side effects are observed after administration of titration dose of varenicline formulations according to recommended schedule due to reduced tolerability. To overcome this problem, the long acting depot formulation of present invention can be administered after one week of oral dosage form to establish tolerance, i.e., after achievement of steady state in 4-7 days. Thus, in an embodiment of present invention, the depot formulation of present invention is administered in combination with the oral administration of varenicline formulation. In a preferred embodiment of present invention, varenicline is administered orally for 1 week followed by administration of depot formulation of present invention once in every two weeks, once a month, twice a month, once in every two months, once in every three months or once every 6 months, such that varenicline is released from depot formulation of present invention at a determined rate. Also provided herein are kits including an orally administered varenicline dosage form component and a depot dosage form component. The prescribing physician may provide the oral dosage component to the patient with the appropriate dosing titration schedule. Upon successful completion of the oral titration, the patient can return to the physician to receive the depot formulation.

In an embodiment, the amount of varenicline or pharmaceutically acceptable salt thereof in the formulation of present invention is about 1% to about 50% w/v of the total depot composition. In preferred embodiment, the amount of varenicline in the formulation of present invention is about 5% to about 40% w/v of the total formulation. In an embodiment, the amount of varenicline in the formulation of present invention is about 30-180 mg varenicline of total formulation. In other embodiments, varenicline is present in an amount form 40-150 mg, 50-140 mg, 60-120 mg, 70-100 mg, or 75-90 mg, relative to the total weight of the formulation.

In one embodiment, the present invention provides a long acting depot formulation comprising a therapeutically effective amount of varenicline or any other pharmaceutically acceptable salt in a depot form suitable for parenteral administration at a medically acceptable location in a subject in need thereof.

Further, the long acting depot formulations of present invention provide equal or superior therapeutic efficacy to the commercially available dosage form, with reduced incidence and/or severity of side effects at the local and/or systemic levels.

The present invention provides long-acting depot formulations comprising varenicline or its pharmaceutically acceptable salt in the form of an aqueous depot suspension injection. According to one embodiment, the pharmaceutical depot formulation is in the form of microspheres, implants, cubosomes, hexosomes, solutions, suspensions, microemulsions, in-situ gelling system and the like, that are suitable for subcutaneous or intramuscular administration of varenicline base or its salts. According to another embodiment, the long acting depot formulation of present invention comprising varenicline or its salts can be delivered by biodegradable or non-biodegradable carrier/s.

In some embodiments, the pharmaceutical depot formulations of the present invention include, but are not limited to, suspensions of varenicline or a pharmaceutically acceptable salt thereof in water, oil or wax phase; poorly soluble polyelectrolyte complexes of varenicline or a pharmaceutically acceptable salt thereof; "in-situ" gel-forming matrices based on the combination of water-miscible solvent with varenicline or a pharmaceutically acceptable salt thereof; and biodegradable polymeric microparticles with incorporated varenicline or a pharmaceutically acceptable salt thereof.

Microspheres, implants and gels are the forms of biodegradable polymeric devices used in prolonging the release of drugs in the body. Besides biodegradable systems, there are non-biodegradable implants and infusion pumps that can be worn outside the body in case if the person shows undesirable side effects due to smoking cessation and nicotine withdrawal. In a preferred embodiment, dosage form with biodegradable polymers can be used, according to present invention.

In certain embodiments, the dosage forms include, but are not limited to, biodegradable injectable depot systems comprising biodegradable polymers such as polylactide (PLA), poly(lactic-co-glycolic acid) (PLGA) 75:25, PLGA 50:50, polycaprolactone (PCL), linear polyhydroxy alkanoate (PHA), polybutylene succinate (PBS), polybutylene succinate adipate (PBSA); polybutylene adipate (PBA); poly-butylene adipate terephthalate (PBAT), polycarbonates, polyurethanes; non-PLGA based injectable depot systems comprising polymers such as ethylene-vinyl acetate (EVA), polyurethane, and injectable biodegradable gels or dispersions.

In particular, the pharmaceutical depot compositions of the present invention are in the form of injectable microparticles wherein the varenicline or pharmaceutically acceptable salt thereof is entrapped in a biodegradable or non-biodegradable carrier. The microparticulate compositions of the present invention may comprise a water-in oil-in water double emulsion.

In embodiment, the present invention provides parenteral pharmaceutical long acting depot compositions of varenicline in an aqueous suspension.

In some embodiments, the varenicline or salt thereof is provided in the depot formulation as particle. In some embodiments, the varenicline or salt thereof can be characterized by a $d_{90}$ of about 0.5 micron to about 10.0 micron, a $d_{50}$ of about 1 micron to about 40 microns and a $d_{90}$ of about 20 microns to about 100 microns. In other embodiments, the size distribution of the varenicline particles in the formulation has a $d_{90}$ of about 1 micron to about 5 microns, a $d_{50}$ of about 5 microns to about 30 microns and a $d_{90}$ of about 40 microns to about 80 microns.

The limited solubility of varenicline base or its salt in water coupled with controlled particle size is utilized for the preparation of long acting depot formulation of present invention.

Depending on the dosage form, the long acting depot formulation of present invention comprises of varenicline or its pharmaceutically acceptable salt and one or more pharmaceutically acceptable excipients selected from fluid containing stabilizer, matrix forming agent, viscosity enhancing agent, one or more of a preservative, a buffer, an isotonizing agent, lipids and the combination thereof. Particular ingredients may function as two or more of these agents simultaneously. e.g. behave like a preservative and a buffer, or behave like a buffer and an isotonizing agent.

The fluid containing stabilizer of the present invention also act as wetting agent or suspending agent and ensure complete wetting of the microparticles by the injection vehicle and thus stabilizing the varenicline base or its pharmaceutically acceptable salt in the composition. Suitable fluid containing stabilizer for use according to the present invention are polyoxyethylene derivatives of sorbitan esters, e.g. polysorbate 20 and polysorbate 80, lecithin, polyoxyethylene ethers, polyoxypropylene ethers, sodium deoxycholate. Preferred wetting agents include polysorbate 20 (Tween 20), polysorbate 40 (Tween 40), and polysorbate 80 (Tween 80). Other fluid containing stabilizer suitable for use include various polymers, low molecular weight oligomers, natural products, and surfactants, including non-ionic and ionic surfactants, such as cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowax 3350® and 1450®, and Carbopol 934® (Union Carbide)), dodecyl trimethyl ammonium bromide, polyoxyethylene stearates, collodial silicon dioxide, phosphates, sodium dodecylsulfate, carboxymethylcellulose calcium, hydroxypropyl celluloses (e.g., HPC, HPC-SL, and HPC-L), methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phosphatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-1100, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2(CON(CH3))\text{-}CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-nonyl β-D-glucopyranoside; octanoyl-N-methylglucamide; n-octyl-β-D-glucopyranoside; octyl β-D-thioglucopyranoside; and the like.

Most of these fluids containing stabilizer are known pharmaceutical excipients and are described in detail in the Handbook of Pharmaceutical Excipients, published jointly by the American Pharmaceutical Association and The Pharmaceutical Society of Great Britain (The Pharmaceutical Society of Great Britain (The Pharmaceutical Press, 1986), specifically incorporated by reference.

The fluid containing stabilizers are present in the formulation of present invention in an amount within the range from about 0.2 to about 10% w/v of total formulation, preferably for about 0.5 to about 5% of the total formulation. Preferably, the amount of fluid containing stabilizer in present invention are from about 0.5 mg to about 30 mg of the total formulation, preferably, about 1 mg to about 20 mg of total formulation.

The matrix forming agent of present composition is selected from polyethylene glycol, sodium carboxymethyl cellulose, hydroxypropyl cellulose, carboxymethyl cellulose, hydroxypropylethyl cellulose, hydroxypropylmethyl cellulose, polyethylene glycols, polyoxyethylene and polyoxypropylene ethers and polyvinylpyrrolidone, with sodium carboxymethyl cellulose and polyvinylpyrrolidone being preferred, although other suitable matrix forming agents may also be used. The preferred matrix forming agent is polyethylene glycol. Suitable liquid crystalline matrix forming agent may be used in present invention such as glyceryl monoleate, glycerylmonostearate and the combinations thereof. The matrix forming agent are present in the formulation of present invention in an amount within the range from about 0.2% to about 10% w/v of total formulation.

The viscosity enhancing agent of present invention that increases the viscosity of the injection vehicle is selected from sorbitol, glycerin, propylene glycol and such other solvents may also be used. The viscosity enhancing agent are present in the formulation of present invention in an amount within the range from about 5% to about 15% w/v of total formulation.

Suitable "in-situ" gel-forming agents of the present invention convert to gels while preparation of the formulation and thus also act as viscosity enhancing agent. Such agents are selected from sucrose acetate isobutyrate, poly N,N-dimethyl acrylamide, poly(methyl vinyl ether), poly (N-vinyl caprolactam), Pluronics, PLGA and PLA. The "in-situ" gel-forming agents are present in the formulation of present invention in an amount within the range from about 40% to about 75% w/w of total formulation.

Pharmaceutically acceptable preservatives are antimicrobials and anti-oxidants used in the present invention which can be selected from the group consisting of benzyl alcohol, benzyl benzoate, methyl paraben, propyl paraben benzoic acid, butylated hydroxyanisole, butylated hydroxytoluene, chlorbutol, a gallate, a hydroxybenzoate, EDTA, phenol, chlorocresol, metacresol, benzethonium chloride, myristyl-γ-piccolinium chloride, phenylmercuric acetate and thimerosal. In particular, methyl paraben and propyl paraben can be used in the range of 0.01%-0.18% w/v of total formulation, benzyl alcohol can be used in the range of 0.5% to 10% w/v of total formulation.

Suitable buffering agents used in present invention are salt of weak acids and should be used in amount sufficient to render the formulation neutral to very slightly basic (up to pH 8.5), preferably in the pH range of 7 to 7.5. Particularly preferred is the use of a mixture of disodium hydrogen phosphate (anhydrous). The pH may also be adjusted by the addition of suitable acids and bases such as sodium hydroxide, hydrochloric acid, glacial acetic acid and the combination thereof.

Pharmaceutically acceptable isotonizing agents used in present invention are, for example, sodium chloride, dextrose, mannitol, sorbitol, lactose, sodium sulfate. The formulation of present invention comprises from 1% to 10% (w/v) isotonizing agent. Preferably, mannitol is used in a concentration from 2% to 7% (w/v), more preferably about 5%. Most preferably, however, from about 1% to about 3% (w/v), especially from about 1.5% to about 2% (w/v) of one or more electrolytes are used to render the suspension isotonic. In addition, electrolytes have the further advantage of buffering the aqueous suspension. Particularly preferred is the use of a mixture of disodium hydrogen phosphate (anhydrous) (typically about 0.9% (w/v)) and sodium dihydrogen phosphate monohydrate (typically about 0.6% (w/v)) for rendering the solution isotonic, neutral and less prone to flocculation of the suspended ester therein. The tonicity adjusting agents adjust the tonicity to preclude toxicity problems and improve biocompatibility. The tonicity adjusting agent of present invention may be selected from, but not limited to sodium chloride, dextrose, potassium chloride, mannitol, and glycerin, although other suitable tonicity adjusting agents may also be used.

Suitable lipids used in the formulation of present invention are capable of forming complex with varenicline or its pharmaceutically acceptable salt such as phosphatidylcholine (PC) or purified egg yolk lecithin, phosphatidylethanolamine (PE), phosphatidylserine (PS), phosphatidylglycerol (PG), phosphatidic acid (PA), phosphatidylinositol (PI), sphingomyelin (SPM), and the like, alone or in combination. Saturated phospholipids such as hydrogenated soy PC may also be used. The phospholipids can be synthetic or derived from natural sources such as egg or soy. In the preferred embodiments, the phospholipids used in the present formulation are dimyristoylphosphatidylcholine (DMPC) and dimyristoylphosphatidylglycerol (DMPG), 1,2-distearoyl-sn-glycero-3-phosphocholine sodium (DSPG-Na), dipalmitoylphosphatidylcholine (DPPC), hydrogenated soya phosphatidyl choline (HSPC), phosphatidyl-N-methylethanolamine (PE-Me), or combinations thereof.

Suitable vehicle used in present invention are water for injection, glycerin and the combinations thereof. Other vehicle used in present invention when the desired dosage form is an oily solution include vegetable oils selected from cottonseed oil, castor oil, sesame oil, arachis oil, oleic acid, ethyl undecanoate, almond oil, coconut oil, olive oil, soybean oil, (purified) tri-glycerides, propylene glycol esters, ethyl oleate, linseed oil, sunflower oil, peanut oil, olive oil, wheat-germ oil and similar oils and the combinations thereof.

The pharmacokinetic properties of the formulations according to the present invention further may depend to a limited extent on the physicochemical properties of the drug, such as the particle size and crystal form.

A particularly desirable feature for an injectable depot composition relates to the ease with which it can be administered. In particular, such an injection should be feasible using a needle as fine as possible in a span of time which is as short as possible. This can be accomplished with the aqueous suspensions of the present invention by keeping the viscosity below about 75 mPa·s, preferably below 60 mPa·s. Aqueous suspensions of such viscosity or lower can both easily be taken up in a syringe (e.g. from a vial), and injected through a fine needle (e.g., a 21 G 1½, 26 G 1, 22 G 2 or 22 G 1¼ needle).

The present invention also provides a process for preparing the long acting depot formulation, which process comprises admixing a pharmaceutically acceptable solvent/s or excipient/s with varenicline or its salts.

In some embodiments, methods used for preparation of the present invention may be selected from high sheer homogenization, high pressure homogenization, Ultrasonication/high speed homogenization, admixture of solvents, solubilizers and actives to prepare suspension, solvent emulsification/evaporation etc. A preferred method is high sheer homogenization. In another embodiment, the method used for particle size reduction of varenicline of present invention may be selected from sonication, cryomilling or other processes inducing high shear in the presence of phospholipid or other membrane-forming amphipathic lipid. A preferred method is cryomilling for particle size reduction of varenicline.

In some embodiments, the long-acting depot composition of varenicline is supplied in an injection volume of 0.5 ml to 2.5 ml in a prefilled vial.

A person skilled in the art for preparing formulations according to the present invention will understand that the proportions of components with respect to each other will vary depending on the specific components used. For example, the use of different solubilizers and stabilizers will require some straightforward modifications to the proportions, depending on the compatibility and miscibility of a particular stabilizer in a particular vehicle.

In embodiments, the excipients for the present invention may be selected from, but not limited to, the range of pharmaceutically acceptable excipients, which are soluble in the aqueous solvent system and which are also compatible with the active ingredient. The excipients selected for the purpose of the present invention do not create any degenerative effect on the active ingredient such as varenicline.

The present invention also provides a method of using the formulation of present invention as an aid in smoking cessation treatment, comprising administering pharmaceutical long acting depot formulation comprising a therapeutically effective amount of varenicline or its pharmaceutically acceptable salt of varenicline.

The present invention also provides a long acting depot formulation for use as an aid in smoking cessation treatment by administering pharmaceutical long acting depot composition comprising a therapeutically effective amount of a pharmaceutically acceptable salt of varenicline.

The present invention also provides a method for reducing nicotine addiction, aiding in the cessation of, or lessening of, tobacco use in a subject by administering a long acting depot formulation comprising varenicline or its pharmaceutically acceptable salt and one or more pharmaceutically acceptable excipients.

The following examples are for the purpose of illustration of the invention only and are not intended in any way to limit the scope of the present invention. In the examples, varenicline as the free base was employed to prepare the depot formulations.

Example 1

Oily Solution

TABLE 1

Composition of oily solution

| Ingredients | Quantity (% w/v) |
|---|---|
| Varenicline | 2%-40% |
| Benzyl benzoate | 10%-50% |
| Benzyl alcohol | 0.5%-10% |
| Cottonseed oil/Castor oil/Sesame oil | qs 0.5%-1.5% |

Procedure:
1. Benzyl benzoate, benzyl alcohol and castor oil/cottonseed oil/sesame oil were mixed.
2. Varenicline was added to the mixture with stirring and heated if required.

Example 2

Varenicline-Lipid Complex Formulation for Intramuscular Injection

TABLE 2

Composition of varenicline- lipid complex formulation

| Ingredients | Quantity (% w/v) |
|---|---|
| Varenicline | 2%-40% w/v |
| Purified egg yolk lecithin | 10%-80% w/v |
| Polysorbate 80 | 0.5%-5% |
| Water | q.s. 0.5 ml-1.5 ml |

Procedure:
1. Purified egg yolk lecithin and varenicline were dissolved in dichloromethane and a thin drug lipid film was prepared using rotary evaporation.
2. Polysorbate 80 was dissolved in water to prepare aqueous phase.

3. The above aqueous phase containing the Polysorbate 80 was added to the varenicline-lipid film and homogenized.

Example 3

Intramuscular (IM) Depot Injection—Microspheres

TABLE 3

Composition of varenicline microspheres

| Ingredients | Quantity (% w/w) |
|---|---|
| Varenicline | 2%-40% |
| *Biodegradable polymer | 60%-95% |

*Biodegradable polymers: PLA, PLGA 75:25, PLGA 50:50, PCL.

Procedure:
1. Varenicline and polymer were dissolved in dichloromethane (organic phase)
2. Polyvinyl alcohol and mannitol were dissolved in the required quantity of water for the external phase.
3. The organic phase of step 1 was added to the external phase of step 2 under continuous homogenization.
4. The above solution/suspension was stirred for 2-3 hrs, and filtered under vacuum.
5. The microsphere powder was washed and dried.
6.

Example 4

Implants

TABLE 4

Composition of varenicline implants

| Ingredients | Quantity (% w/w) |
|---|---|
| Varenicline | 2%-40% |
| *Biodegradable/Non biodegradable polymer | 60%-95% |

Biodegradable polymers: PLA, PLGA 75:25, PLGA 50:50, PCL.
Non biodegradable polymer: EVA, Polyurethane Procedure:
1. Varenicline and polymer were cryomilled.
2. The polymer-varenicline powder mixture was introduced into hot melt extruder.
3. The extrudes were then cut to desired length.

Example 5

Liquid Crystalline Systems (Cubosomes/Hexosomes)

TABLE 5

Composition of varenicline cubosomes/hexosomes

| Ingredients | Quantity (% w/v) |
|---|---|
| Varenicline | 2%-40% |
| Glyceryl mono-oleate/Glyceryl monostearate | 80%-90% |
| Polysorbate 80 | 0-5% |

Procedure:
1. Glyceryl mono-oleate/Glyceryl monostearate and polysorbate 80 were dissolved in water under stirring.
2. Varenicline was added to the above mixture.
3. After complete addition of varenicline, the mixture was vortexed.

Example 6

In Situ Gelling System

TABLE 6

Composition of in-situ gelling system

| Ingredients | Quantity (% w/v) |
|---|---|
| Varenicline | 2%-40% |
| Sucrose acetate isobutyrate (SAIB) | 40%-75% |
| Ethanol | 2%-5% |
| Glycerin | 5%-15% |

Procedure:
1. Sucrose acetate isobutyrate, ethanol and glycerin were mixed under stirring.
2. Varenicline was added to the above mixture and stirred till a homogenous mixture is formed.
3. The mixture was heated only if required.

Example 7

In Situ Gelling System

TABLE 7

Composition of in-situ gelling system

| Ingredients | Quantity (% w/v) |
|---|---|
| Varenicline | 2%-40% |
| N-methyl-2-pyrollidone | 10%-25% |
| *Biodegradable polymer | 2%-5% |

Biodegradable polymers: PLA, PLGA 75:25, PLGA 50:50, PCL.

Procedure:
1. Varenicline and polymer were mixed in N-methyl-2-pyrollidone under stirring.
2. The above mixture was stirred till a homogenous mixture was formed.
3. The mixture was heated only if required.

Example 8

Aqueous Suspension

TABLE 8

Composition of aqueous suspension

| Ingredients | Quantity (% w/v) |
|---|---|
| Varenicline | 2%-40% |
| Sodium carboxy methylcellulose | 1%-3% |
| Polysorbate 80 | 0.5%-5% |
| Benzyl alcohol | 0.5%-1% |
| Water | qs 0.5 ml-1.5 ml |

Procedure:
1. Sodium carboxy methylcellulose, polysorbate 80 and benzyl alcohol were dissolved in required quantity of water under stirring.
2. Varenicline was added to solution of step 1 and stirred till a homogenous suspension is formed.

3. The volume was made up with water, if required.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to fall within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "an excipient" includes a single excipient as well as two or more different excipients, and the like.

We claim:

1. A kit, comprising a syringe filled with a pharmaceutical long-acting depot composition comprising varenicline, or a pharmaceutically acceptable derivative thereof, and one or more pharmaceutically acceptable excipients,
    wherein the amount of varenicline in the composition is from about 30 mg to about 180 mg, and
    wherein the volume of the composition is from 0.5 ml to 2.5 ml.

2. The pharmaceutical long-acting depot composition according to claim 1, wherein the particle size ($d_{90}$) of varenicline in the composition is from about 20 microns to about 100 microns.

3. The pharmaceutical long-acting depot composition according to claim 1, wherein the particle size ($d_{90}$) of varenicline in the composition is from about 40 microns to about 80 microns.

4. A pharmaceutical long-acting depot composition wherein the composition comprises varenicline, or a pharmaceutically acceptable derivative thereof, and one or more pharmaceutically acceptable excipients dispersed in biodegradable carrier, said carrier in the form of microspheres, implants, cubosomes, hexosomes, solutions, suspensions, microemulsions, in-situ gelling system, or a combination thereof.

5. The pharmaceutical long-acting depot composition according to claim 4, wherein the biodegradable carrier comprises polylactide (PLA), poly(lactic-co-glycolic acid) (PLGA) 75:25, PLGA 50:50, polycaprolactone (PCL), linear polyhydroxy alkanoate (PHA), polybutylene succinate (PBS), polybutylene succinate adipate (PBSA), polybutylene adipate (PBA), polybutylene adipate terephthalate (PBAT), polycarbonates, polyurethanes, ethylene-vinyl acetate (EVA), polyurethane, or combination thereof.

6. The pharmaceutical long-acting depot composition according to claim 1, wherein the composition comprises varenicline, or a pharmaceutically acceptable derivative thereof, and one or more pharmaceutically acceptable excipients dispersed in non-biodegradable carrier is in the form of implants and infusion pumps.

7. The pharmaceutical long-acting depot composition according to claim 1, wherein the one or more pharmaceutically acceptable excipients are selected from stabilizers, matrix forming agents, lipids, viscosity enhancing agents, preservatives, buffering agents, isotonizing agents, injection vehicles, and combinations thereof.

8. The pharmaceutical long-acting aqueous depot composition according to claim 7, wherein the stabilizer is selected from polyoxyethylene derivatives of sorbitan esters, lecithin, polyoxyethylene ethers, polyoxypropylene ethers, sodium deoxycholate in an amount from about 0.2% to about 10% w/v of the total formulation.

9. The pharmaceutical long-acting aqueous depot composition according to claim 7, wherein the matrix forming agent is selected from polyethylene glycol, sodium carboxymethyl cellulose, hydroxypropyl cellulose, carboxymethyl cellulose, hydroxypropylethyl cellulose, hydroxypropylmethyl cellulose, polyethylene glycols, polyoxyethylene and polyoxy-propylene ethers and polyvinylpyrrolidone, with sodium carboxymethyl cellulose and polyvinylpyrrolidone in an amount from about 0.2% to about 10% w/v of total formulation.

10. The pharmaceutical long-acting aqueous depot composition according to claim 7, wherein the lipid is selected from phosphatidylcholine, purified egg yolk lecithin, phosphatidylethanolamine, phosphatidylserine, phosphatidylglycerol, phosphatidic acid, phosphatidylinositol, sphingomyelin, hydrogenated soy phosphatidylcholine, dimyristoylphosphatidylcholine, dimyristoylphosphatidylglycerol, 1,2-distearoyl-sn-glycero-3-phosphocholine sodium, dipalmitoylphosphatidylcholine, hydrogentated hydrogenated soya phosphatidyl choline, phosphatidyl-N-methylethanolamine, and combinations thereof.

11. The pharmaceutical long-acting aqueous depot composition according to claim 7, wherein the viscosity enhancing agent is selected from sorbitol, glycerin, propylene glycol or combination thereof from about 5% to about 15% w/v of the total formulation.

12. The pharmaceutical long-acting aqueous depot composition according to claim 7, wherein the preservative is selected from benzyl alcohol, benzyl benzoate, methyl paraben, propyl paraben benzoic acid, butylated hydroxyanisole, butylated hydroxytoluene, chlorbutol, a gallate, a hydroxybenzoate, EDTA, phenol, chlorocresol, metacresol, benzethonium chloride, myristyl-γ-piccolinium chloride, phenylmercuric acetate and thimerosal in an amount from about 0.5% to about 10% w/v of total formulation.

13. The pharmaceutical long-acting aqueous depot composition according to claim 7, wherein the vehicle is selected from water for injection, glycerin vegetable oil, oleic acid, ethyl undecanoate, almond oil, coconut oil, olive oil, soybean oil, (purified) triglycerides, propylene glycol esters, ethyl oleate, linseed oil sunflower oil, peanut oil, olive oil, wheat-germ oil and combinations thereof.

14. The pharmaceutical long-acting depot composition according to claim 1, wherein the composition is an aqueous suspension comprising varenicline, or a pharmaceutically acceptable derivative thereof, and one or more pharmaceutically acceptable excipients selected from CMC, polysorbate 80, benzyl alcohol, or a combination thereof.

15. A method of aiding a patient with smoking cessation comprising administrating to the patient a long-acting depot formulation comprising 30-180 mg varenicline, or a pharmaceutically acceptable derivative thereof, and one or more pharmaceutically acceptable excipients dispersed in biodegradable carrier, said carrier in the form of microspheres, implants, cubosomes, hexosomes, solutions, suspensions, microemulsions, in-situ gelling system, or a combination thereof, wherein the one or more pharmaceutically acceptable excipients comprise suspending agents, wetting agents, preservatives, buffering agents, viscosity enhancing agents, density enhancing agents, injection vehicles, isotonizing agents, or a combination thereof.

16. The method of claim 15, wherein the composition is administered subcutaneously or intramuscularly.

17. The method of claim 15, wherein the composition is administered bimonthly or monthly.

* * * * *